United States Patent
Xue et al.

[11] Patent Number: 6,151,383
[45] Date of Patent: Nov. 21, 2000

[54] RADIOGRAPHIC TESTING SYSTEM WITH LEARNING-BASED PERFORMANCE PREDICTION

[75] Inventors: Ping Xue, Waukesha, Wis.; Richard Aufrichtig, Mountain View, Calif.; Michael Andrew Juhl, Waukesha, Wis.

[73] Assignee: General Electric Company, Milwaukee, Wis.

[21] Appl. No.: 09/224,242

[22] Filed: Dec. 30, 1998

[51] Int. Cl.[7] .................................................. H05G 1/44
[52] U.S. Cl. .............................................. 378/108; 378/97
[58] Field of Search .................................. 378/108, 98.8, 378/97, 207

[56] References Cited

U.S. PATENT DOCUMENTS 5,751,783   5/1998   Granfors et al. .................. 378/108
5,949,848   9/1999   Gilblom ............................. 378/98.8

*Primary Examiner*—David P. Porta
*Attorney, Agent, or Firm*—Craig A. Fieschko, Esq.; DeWitt Ross & Stevens S.C.; Phyllis Y. Price

[57] ABSTRACT

Disclosed herein is a radiographic imaging system which performs system performance monitoring by (1) using automatic exposure control (AEC) components to predict the average image gray level; (2) obtaining measured average image gray levels from the portions of the X-ray detector situated in the X-ray shadow of the AEC components; and then (3) comparing the predicted and measured values. The predicted values are determined by use of a prediction model which is modified by a learning system over successive exposures to provide more accurate predictions. After the learning system has sufficiently developed the prediction model, the error between the predicted and measured gray level values may be monitored in later exposures and an error routine can be activated if the error exceeds a predetermined threshold. In this case, the error may indicate that system components in the imaging chain (e.g., the detector or AEC components) require maintenance.

15 Claims, 2 Drawing Sheets

RADIOGRAPHIC TESTING SYSTEM WITH LEARNING-BASED PERFORMANCE PREDICTION

FIELD OF THE INVENTION

This disclosure concerns an invention relating generally to radiographic imaging systems, and more specifically to radiographic imaging systems which perform diagnostic system performance monitoring and reporting.

BACKGROUND OF THE INVENTION

The classic radiographic or "X-ray" image is obtained by situating an object to be imaged between an X-ray emitter and an X-ray detector. Emitted X-rays pass through the object to strike the detector, with the response of the detector varying over its area as a function of the intensity of the incident X-rays. Since the intensity of the X-rays incident on the detector is largely a function of the density of the object along the path of the X-rays, the detector receives a shadow image of the object which may then be viewed and analyzed by X-ray technicians, e.g., radiologists. In the case of analog radiographic systems, the detector is formed of X-ray film, whereas digital radiographic systems have solid-state detector components (e.g., scintillator/photodiode arrays) whereby the image is provided in electronic form.

It is common in both analog and digital radiographic systems to incorporate automatic exposure controls (AEC) which deactivate the X-ray emitter when a predetermined X-ray dose is delivered to the object, and/or when the X-ray detector has achieved the optimal optical density/signal-to-noise ratio for imaging. The AEC generally provides a dose monitor within the path of the emitted X-rays wherein an array of dose sensors (e.g., ion chambers) is located across the dose monitor's area. Like the X-ray detector, these dose sensors receive the emitted X-rays and provide a response which varies as a function of the intensity of the incident X-rays. The response signals from the dose sensors can be compared to reference measurements in the AEC controller, and if the dose sensor signals reach or exceed reference thresholds, the AEC controller signals the X-ray emitter to cease X-ray emission. During this process, the AEC controller takes into account the settings of the emitter (its voltage/current, etc.), positioning parameters (the location of the emitter, its radiation field size/collimation, etc.), and other such variables so as to provide desirable reference thresholds for the conditions at hand.

FIG. 1 illustrates an exemplary arrangement of this type in greater detail, wherein an object 10 to be imaged is situated between an X-ray emitter 12 and an X-ray detector 14, and wherein a dose monitor 16 is situated in front of the detector 14 (though it is noted that a dose monitor may be provided within the detector itself rather than separately). The dose monitor 16 communicates with an AEC controller 18, which in turn communicates with the emitter 12 and with a workstation 20 which may include system controls, image acquisition and processing apparata, display apparata for the image, etc. FIG. 2 then illustrates the detector 14 and dose monitor 16 in greater detail, with the dose monitor 16 being depicted as an ion chamber having a number of dose sensors (ion chamber cells) 22, 24, and 26 whose signals may be selectively summed in a preamplifier 28 to provide an integrated dose monitor signal 30 for comparison with the reference measurements. Selective summing of the dose sensor signals is used because only certain sensors may be active depending on the type of imaging application at hand; for example, a standard posteroanterior (PA) chest projection imaging application might select left and right sensors 22 and 26 and deselect the central sensor 24, whereas a lateral chest exam imaging application might select only the central sensor 24 and deselect the left and right sensors 22 and 26. The deselected sensors are not used for determining the proper exposure time in the imaging application being applied because they may not provide an accurate dose measurement at the area of interest.

In digital radiographic systems, the AEC arrangement might be useful for purposes other than simply setting a desired exposure time. If a digital X-ray detector is correctly calibrated, the mean gray level of an image is proportional to the entrance exposure of the detector. Since the dose monitor also rests within the path of the X-rays, the mean image gray level should also be proportional to the dose monitor exposure. Therefore, one might be able to use the dose monitor exposure to predict the mean image gray level of the detector. If the predicted mean gray level is then compared to the actual mean gray level and is found to have a significant prediction error, this can indicate that the performance of the imaging system is diminished somewhere along the imaging chain (i.e., in the detector and/or dose monitor, etc.) and that recalibration or other maintenance is required. Thus, one might be able to utilize the dose monitor to effect a convenient monitoring system for system performance.

However, such a performance monitoring system would not work well in most radiographic imaging applications because the dose monitor and detector responses are functions of X-ray beam quality. If the X-ray beam quality changes between the dose monitor and detector owing to different imaging applications or owing to the qualities of the X-rayed object, the dose monitor will obviously not provide an accurate prediction of the mean image gray level of the detector. As an example, X-rayed objects having different sizes, shapes, and materials will produce different amounts of X-ray scatter, and the scattered X-rays will strike the dose monitor and detector to different degrees and in different locations. Further, unless the X-ray beam is of ideal quality (i.e., uniform intensity over its area), different dose monitor sensors may receive different amounts of radiation. As a result, the "averaging" provided by the selective summing process may not allow the correct prediction of mean image gray level. Therefore, it is impossible to calibrate the AEC to accurately predict mean detector image gray level for all applications, and a performance monitoring system such as the one described above will only work in idealized situations.

SUMMARY OF THE INVENTION

The invention, which is defined by the claims set out at the end of this document, is directed to a method of evaluating the performance of a radiographic imaging system of the type which includes an X-ray emitter, a dose monitor having multiple dose sensors therein (e.g., an ion chamber with multiple cells), and an X-ray detector. A brief summary of an exemplary version of the invention will now be provided.

When the system is configured to execute a particular type of imaging application (e.g., a chest PA exam), certain dose sensors within the dose monitor are selected for automatic exposure control purposes: when these selected dose sensors indicate that a predetermined exposure threshold has been met, the exposure is terminated. These same dose sensors may be used to calculate a predicted average image gray level by using their signals in a prediction model, the form of which is predetermined prior to initially calculating the predicted average image gray level. A measured average image gray level is also determined from the areas on the detector corresponding to the selected dose sensors (i.e., those areas on the detector which are in the X-ray shadow of the selected dose sensors).

The difference between the predicted and measured average image gray levels can then be calculated to determine the error in the prediction. If the error is greater than a predetermined threshold, an error routine may be activated (e.g., the technician operating the system may be instructed to run diagnostic tests or to perform system maintenance). However, in order to obtain superior system performance monitoring characteristics, the system preferably incorporates a learning system whereby the prediction model is repeatedly updated over several exposures to enhance its accuracy, i.e., to reduce the error in the predicted average image gray level. This reduces the probability that the error routine may be spuriously initiated. As an example of how the learning system may update the prediction model, it may store the errors generated between the predicted and measured average image gray levels with each exposure, and it may utilize regression techniques to alter the mathematical coefficients of the prediction model after each exposure is completed. Alternatively, the operating parameters for the selected dose sensors may be stored in a look-up table/matrix along with the measured average image gray levels, thereby allowing predictions to be made by using the dose sensor parameters at hand to look up or interpolate gray levels.

After the prediction model has been updated a sufficient number of times that its results are believed to be accurate, the updating can be halted to calibrate the prediction model in a fixed state. As an example, the learning system could be left to operate for some number of exposures N before the prediction model is fixed. Alternatively, the prediction model could be fixed after it results in errors below some predetermined threshold value for one or more exposures. The aforementioned error routine is preferably not enabled until this calibration occurs, so that it will be activated only after the prediction model produces an error above some preset threshold. By waiting until the prediction model is fully developed before enabling the error routine, the system avoids spurious activation of the error routine while it is still learning how to accurately predict the average image gray level.

Further advantages, features, and objects of the invention will be apparent from the following detailed description of the invention in conjunction with the associated drawings.

DETAILED DESCRIPTION OF PREFERRED EMBODIMENTS OF THE INVENTION

Figure 1:
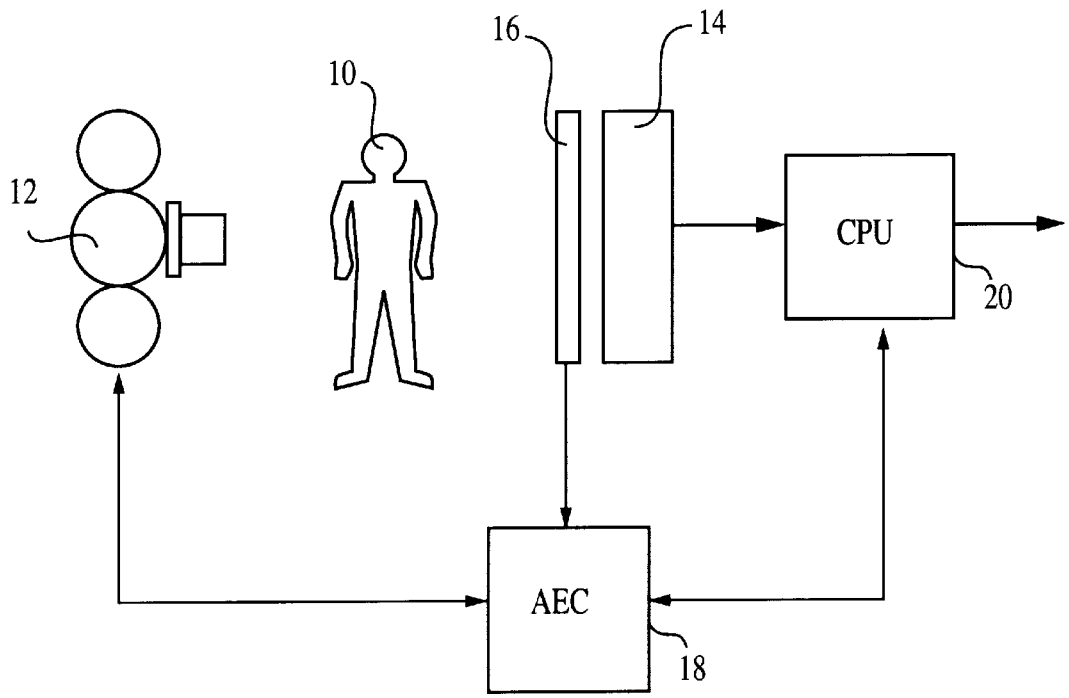
FIG. 1 is a schematic diagram depicting a digital radiographic imaging system with automatic exposure controls (AEC).
Figure 2:
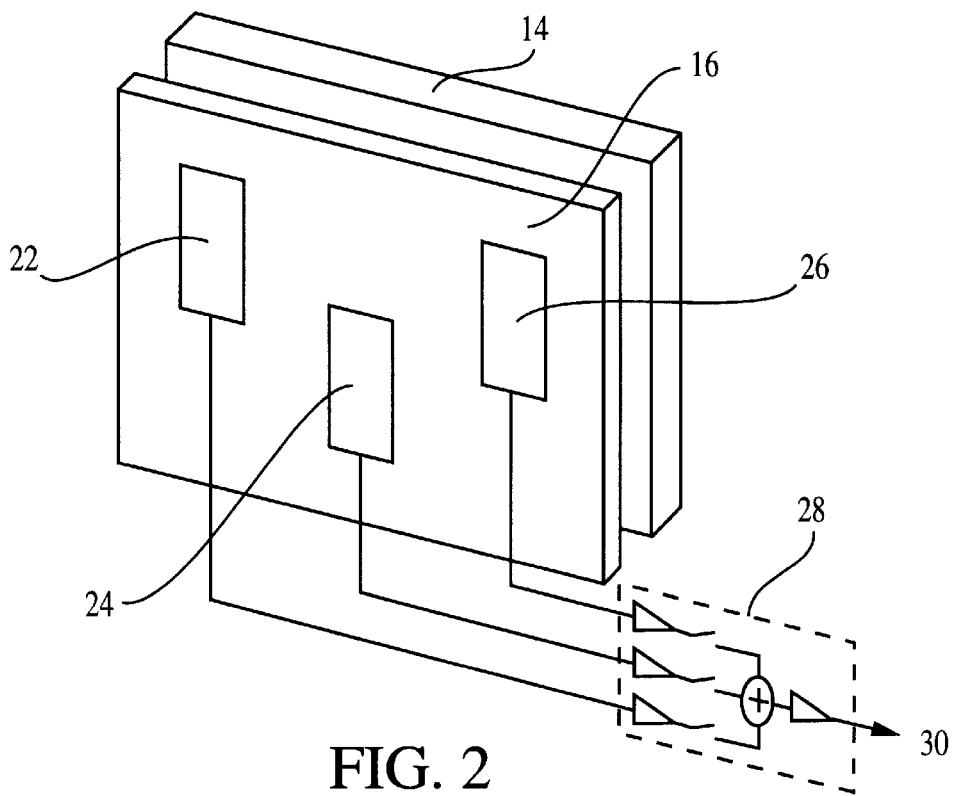
FIG. 2 is a front perspective view of the dose monitor and X-ray detector of FIG. 1.
Figure 3:
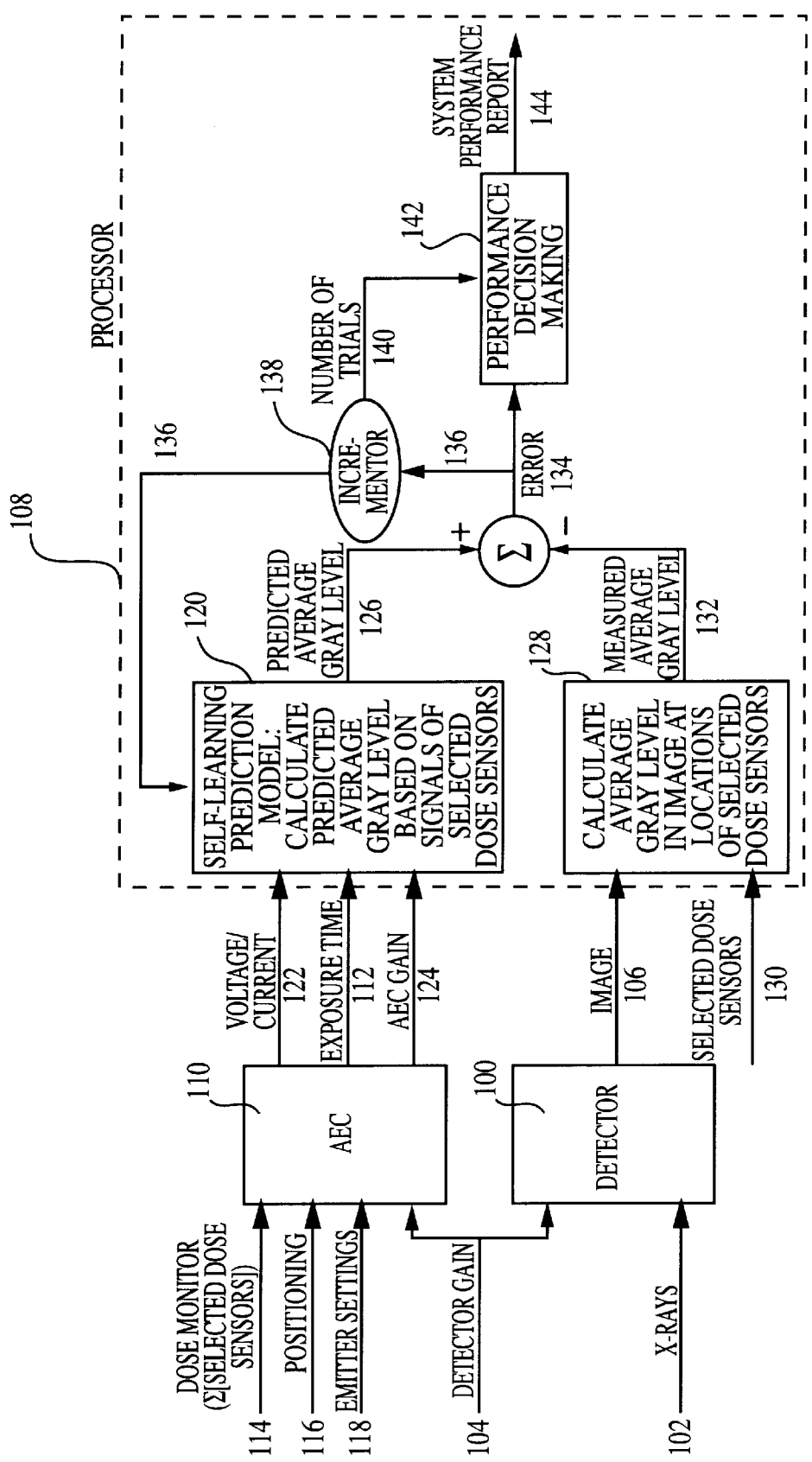
FIG. 3 is a flow chart of the process of the present invention illustrating use of AEC components to monitor and report performance of the radiographic imaging system along the imaging chain.

An exemplary process of the testing system of the present invention is illustrated by the flow diagram of FIG. 3. Within the process, certain procedures are conventional within a radiographic imaging system: for example, an X-ray detector 100 utilizes the incident X-rays 102 and the detector gain settings 104 to provide image data 106 to a processor 108, and an automatic exposure controller (AEC) 110 provides an exposure shutoff time 112 to the processor 108 based on inputs such as dose monitor signals 114 (i.e., integrated signals from selected dose sensors), emitter positioning parameters 116, emitter X-ray generator settings 118 (voltage/current, etc.), and the detector gain settings 104. As described above with reference to FIGS. 1 and 2, the exposure shutoff time 112 determined by the AEC 110 is utilized to terminate the exposure when a desired radiation dose has been delivered, but this AEC shutoff process is not illustrated in FIG. 3. Further, the processor 108 is generally used to analyze the image data 106, provide it in a desired output format, or otherwise manipulate it, a process which is also not illustrated in FIG. 3.

Within the testing system, the processor 108 performs several novel additional steps which may be summarized as follows:

1. Calculate a predicted average image gray level by using the dose monitor signals in a prediction model: In this step, which is depicted by the process block 120 in FIG. 3, signals from the AEC 110 (e.g., its voltage/current 122, calculated exposure shutoff time 112, AEC gain 124, etc.) are used to calculate a predicted average image gray level 126 for the image 106 based on the X-ray exposure of the dose sensors that were active during the exposure. As an example, with reference to FIG. 2, if only the left and right dose sensors 22 and 26 are selected within the dose monitor 16 during an imaging application, only the signals from these dose sensors 22 and 26 are averaged by the preamplifier 28 and used by the prediction model 120 in the calculation of the predicted average gray level 126. As will be discussed in greater detail below, when the imaging system initially begins obtaining exposures for a given imaging application, the prediction model used by process block 120 is entirely predefined (e.g., it will have predetermined coefficients). However, for subsequent exposures, a self-learning routine will update the prediction model (e.g., revise its coefficients) so that it becomes more accurate. Prior to further discussion of this self-learning feature, it will be helpful to further discuss the prediction model of process block 120.

The prediction model, which relates the exposure level on the selected dose sensors of the dose monitor to the exposure level on the detector, may take any appropriate mathematical form desired by one of ordinary skill in the art of radiographic imaging. Since it will generally vary between different imaging systems and also between different imaging applications and conditions, it should be kept in mind that the processor 108 may actually contain several prediction models, and will access the appropriate one when it detects that a particular imaging application and a particular set of conditions is present. The form of the prediction model to be applied in any given situation (as well as the coefficients of the model) might be defined by past practice, or by performing several empirical tests and applying regression (linear or nonlinear) to establish the model's initial behavior. Alternatively, keeping in mind that the learning system of the invention will update the prediction model to improve its accuracy, the coefficients could simply be estimated model values which are expected to be refined in later updates.

2. Calculation of a measured average image gray level in the detector image at the locations of the selected dose sensors: As may be best visualized with reference to FIG. 2, certain sections of the detector 14 rest within the X-ray shadow of the dose sensors 22, 24, and 26. Since only certain dose sensor signals were used to calculate the predicted average image gray level, for purposes of comparison, it will now be useful to have the processor 108 calculate a measured average image gray level from the areas on the detector 14 which correspond to the selected sensors. These areas are easily determined because the relative locations of the sensors and the detector are fixed, and the image data 106 contains location data for each pixel as well as its gray level; therefore, calculation of the measured average image gray level corresponding to the sensor locations is simply a matter of averaging the gray levels of the pixels located in the shadow of the selected sensors. This routine is represented in FIG. 3 by the process block 128, wherein the image data 106 and the location/selection of the dose sensors 130 is used to calculate the measured average gray level 132 in the image.

3. Calculation of the difference between the measured average gray level 132 and the predicted average gray level 126: The error 134 between the predicted average gray level and the measured average gray level 132 is then determined.

4. Updating the prediction model to reduce the error in subsequent predictions: As illustrated by line 136, the error 134 is supplied to the self-learning system 120 so the prediction model may be updated. As an example, this may be done by applying regression to the current error 134 and prior errors, and then using the results of the regression to modify the coefficients of the prediction model.

5. After N exposures, ceasing further updates and calibrating the prediction model into a fixed state: The rationale behind this optional step is that at some point, it may be desirable to disable the self-learning feature of process block 120 to fix the coefficients of the prediction model at a constant level. As an example, after some number of exposures N, the prediction model might be considered sufficiently "settled" with minimal error that further updates are not necessary. This is illustrated in FIG. 3 by the incrementor 138, which counts the number of exposures 140 and then disables the self-learning feature of block 120 (i.e., ceases updates) after some predetermined number of exposures N is reached. Alternatively, the incrementor 138 of FIG. 3 could function by disabling the self-learning feature once the error 134 falls below some predetermined threshold, indicating that the accuracy of the prediction model 120 is sufficiently accurate that further updates are unnecessary.

6. Reporting of system performance: The error 134 may be supplied to a performance decision-making routine 142 which may report the error, error history/trends, etc., and which may issue some sort of performance report or error routine 144 when the error 134 exceeds some predetermined threshold. Since the error 134 may be higher during initial exposures when the coefficients of the prediction model 120 have undergone relatively few updates, it may be beneficial to prevent initiation of an error report/routine 144 until the performance decision-making routine 142 determines that a certain number N of trials 140 has occurred (e.g., until the prediction model is calibrated into a fixed state as discussed above).

It should be understood that a preferred embodiment of the invention is described above to illustrate different possible features of the invention, and that these features may be combined in different ways. Apart from combining the different features of the above-described embodiment in varying ways, other modifications are also considered to be within the scope of the invention. Following is an exemplary list of such modifications.

First, in the self-learning prediction model 120, it is also possible that for any given imaging application and set of conditions, the process block 120 will initially begin with several different prediction models having initial model coefficients. For example, for a PA chest exam taken under certain imaging conditions, the block 120 may start with several different prediction models having different forms. As subsequent exposures are made, the self-learning feature of the invention may update the coefficients of each of the different prediction models, and will eventually eliminate the less accurate models to retain only the most accurate model (or models). The most accurate model may then be fixed for use in later exposures taken under the same general imaging conditions.

Second, when multiple prediction models compete as described above, it is also possible that even once the "best" prediction model is fixed within the self-learning system, other proposed prediction models may be tested in parallel with the fixed prediction model every time a new exposure is made. If one of the proposed prediction models should later show less error over the long run than the fixed prediction model, the fixed model can be replaced.

The invention is not intended to be limited to the preferred embodiments described above, but rather is intended to be limited only by the claims set out below. Thus, the invention encompasses all alternate embodiments that fall literally or equivalently within the scope of these claims.

What is claimed is:

1. A method of evaluating the performance of a radiographic imaging system, the system including an X-ray emitter, a dose monitor having multiple dose sensors therein, and an X-ray detector, wherein X-rays coincident on each dose sensor are also coincident on corresponding areas on the detector, the method comprising:
    a. selecting one or more dose sensors,
    b. activating the X-ray emitter, and
    c. calculating an average image gray level, the average image gray level being calculated from the areas on the detector corresponding to the selected dose sensors.

2. The method of claim 1 further comprising the step of deactivating the X-ray emitter when the selected dose sensors indicate that a predetermined exposure threshold has been met.

3. The method of claim 1 further comprising the step of calculating a predicted average image gray level, the predicted average image gray level being calculated from the selected dose sensors in accordance with a predetermined prediction model.

4. The method of claim 3 further comprising the step of calculating the difference between the average image gray level and the predicted average image gray level.

5. The method of claim 4 further comprising the step of updating the prediction model to reduce the difference.

6. A method comprising:
    a. repeatedly performing the method of claim 5 N times, where N is an integer number greater than 1;
    b. subsequently performing the method of claim 5 without updating the prediction model, thereby calibrating the prediction model into a fixed state.

7. The method of claim 6 wherein N is a predetermined number.

8. The method of claim 6 wherein N is reached when the difference between the average image gray level and the predicted average image gray level is below a predetermined threshold.

9. The method of claim 6 further comprising the subsequent steps of:
    a. activating the X-ray emitter;

b. calculating an average image gray level, the average image gray level being calculated from the areas on the detector corresponding to the selected dose sensors;

c. calculating a predicted average image gray level, the predicted average image gray level being calculated from the selected dose sensors in accordance with the calibrated prediction model;

d. calculating the difference between the average image gray level and the predicted average image gray level; and e. initiating an error routine when the difference exceeds a predetermined threshold.

10. A method of evaluating the performance of a radiographic imaging system, the system including an X-ray detector and a dose monitor having multiple dose sensors therein, wherein X-rays coincident on each dose sensor are also coincident on corresponding areas on the detector, the method comprising:

a. calculating a predicted average image gray level, the predicted average image gray level being calculated from selected dose sensors;

b. calculating an average image gray level, the average image gray level being calculated from the areas on the detector corresponding to the selected dose sensors, and c. calculating the difference between the predicted average image gray level and the average image gray level.

11. The method of claim 10 further comprising the step of initiating an error routine when the difference exceeds a predetermined threshold.

12. The method of claim 10 wherein:

the calculation of the predicted average image gray level utilizes a predetermined prediction model, and wherein the prediction model is updated to reduce the difference after the difference is calculated.

13. A method comprising:

a. repeatedly performing the method of claim 12 N times, where N is an integer number greater than 1;

b. subsequently performing the method of claim 12 without updating the prediction model, thereby calibrating the prediction model into a fixed state.

14. The method of claim 13 wherein N is a predetermined number.

15. The method of claim 13 wherein N is reached when the difference between the average image gray level and the predicted average image gray level is below a predetermined threshold.

* * * * *